United States Patent [19]

Gassman et al.

[11] 4,188,325
[45] Feb. 12, 1980

[54] ISATIN PROCESS AND PRODUCTS

[75] Inventors: Paul G. Gassman, St. Paul, Minn.; Berkeley W. Cue, Jr., Groton, Conn.

[73] Assignee: Regents of University of Minnesota, Minneapolis, Minn.

[21] Appl. No.: 935,687

[22] Filed: Aug. 21, 1978

Related U.S. Application Data

[62] Division of Ser. No. 787,992, Apr. 15, 1977.

[51] Int. Cl.² ............................................. C07D 209/34
[52] U.S. Cl. .................................. 260/325 R; 260/323
[58] Field of Search ................... 260/325 R, 326.12 R

[56] References Cited

U.S. PATENT DOCUMENTS

| | | | |
|---|---|---|---|
| 2,335,273 | 11/1943 | Haller | 260/325 R |
| 2,642,439 | 6/1953 | Coles | 260/325 R |
| 3,632,587 | 1/1972 | Hollowood | 260/325 R |
| 4,020,179 | 4/1977 | Irvine | 260/325 R |

OTHER PUBLICATIONS

Yale, Jour. of Med. & Pharm. Chemistry, vol. 1, No. 2, (1959), pp. 121–133.

*Primary Examiner*—Nicholas S. Rizzo
*Attorney, Agent, or Firm*—Gordon W. Hueschen

[57] ABSTRACT

An aniline is converted to a 3-lower hydrocarbonthiooxindole by processes already known in the art, the product converted to a 3-halo-3-lower hydrocarbonthiooxindole by oxidative halogenation, and the product subjected to hydrolysis to form the desired isatins.

25 Claims, No Drawings

ISATIN PROCESS AND PRODUCTS

The invention described herein was made in part in the course of work under a grant or award from the Department of Health, Education, and Welfare.

This is a division of application Ser. No. 787,992, filed Apr. 15, 1977.

BACKGROUND OF THE INVENTION

The invention is directed to a process for preparing isatins and to novel compounds produced therein, and is particularly directed to processes in which isatins can be prepared from anilines with a wide variety of substituents.

Isatins have long been considered as valuable synthetic intermediates in the preparation of both pharmaceuticals and dyes. See, for example, the chapter on Indigoid Dyes, pp. 551-576, *The Chemistry of Synthetic Dyes*, Reinhold Publishing Co., New York, N.Y. (1955). As a consequence, considerable effort has been devoted to developing useful synthetic approaches to the preparation of this class of compound from readily available starting materials, particularly the anilines. Unfortunately, the processes heretofore available were limited in regard to the type of substituents which could be present in the starting anilines due to the fact that such processes required catalysis by strong acids. Thus, Sandmeyer, *Helv. Chem. Acta*, 2, 234 (1919) discloses a process in which aniline is reacted with trichloroacetaldehyde and then with hydroxylamine in base. The resulting isonitrosoacetanilide is then heated in sulfuric acid. Also, Stolle, *J. Prakt. Chem.*, 105, 137 (1922) discloses a process in which an aniline is treated with oxalyl chloride followed by Friedel-Crafts type acylation in the presence of a strong Lewis acid. Since both methods require electrophilic attack on the aromatic ring, the presence of strong electron-withdrawing groups in the aniline, especially in the meta position, tend to inhibit the reaction. For example, a nitro group in the meta position effectively blocks these syntheses.

OBJECTS OF THE INVENTION

It is an object of the invention to provide a new and improved process for making isatins from anilines. It is a further object of the invention to provide such process which can tolerate a broad spectrum of electron-withdrawing and electron-donating substituents on the aniline. It is a further object of the invention to provide new and useful isatins and intermediates. It is a further object of the invention to avoid the disadvantages of the prior art and to obtain advantages as will appear as the description proceeds.

BRIEF DESCRIPTION OF THE INVENTION

The invention is directed to a process for making isatins by subjecting a 3-lower hydrocarbonthiooxindole to oxidative halogenation to form a 3-halo-3-lower hydrocarbonthiooxindole and then subjecting the latter to hydrolysis to form the desired isatin.

The starting compounds in this process may be prepared from anilines by first converting the aniline to an N-haloaniline by oxidative halogenation with a source of positive halogen as described in U.S. Pat. No. 3,972,894, reacting the formed N-haloaniline with a β-lower hydrocarbonthiocarboxylic ester or β-lower hydrocarbonthiocarboxylic amide to form the azasulfonium salt, and rearranging the latter to form a 2-(lower hydrocarbonthio-carboxymethyl) aniline in which the carboxy group is in the form of an ester or amide. The resulting substituted anilines are then cyclized by heating to form the desired 3-lower hydrocarbonthiooxindole starting compound.

The first step of the process of the invention, namely, the conversion of the starting 3-lower hydrocarbonthiooxindole to 3-halo-3-lower hydrocarbonthiooxindole, is effected by the oxidative halogenation of the starting compound. This is a well known unit process applied to non-analogous starting compounds in which the starting compound is reacted with N-chlorosuccinimide or N-bromosuccinimide, or like sources of active halogen, such as molecular chlorine, tert butyl hypochlorite, calcium hypochlorite, sodium hypochlorite, and the bromo analogs thereof which, in the reaction yield up positive halogen atoms. See, for example, U.S. Pat. No. 3,972,894, Gassman, et al., *J. Am. Chem. Soc.*, 96, 3002 (1974); and Gassman, et al., *Tetrahedron Letters*, 3463 (1974) for the application of oxidative chlorination to non-analogous starting materials. It will ordinarily be sufficient to bring the reagents together, advantageously in an inert solvent, with or without heating and to allow the reaction to proceed until the desired oxidative halogenation is obtained.

It has been found in accordance with the invention that the oxidative halogenation can be applied to the starting 3-lower hydrocarbonthiooxindoles with a large spectrum of electron-withdrawing and electron-donating substituents. Processes applicable for the conversion of anilines with such a wide spectrum of electron-withdrawing and electron-donating substituents to the desired 3-lower hydrocarbonthiooxindoles are described in U.S. Pat. No. 3,972,894; Gassman and van Bergen, *J. Am. Chem. Soc.*, 96, 5508 (1974), and Gassman et al., *J. Am. Chem. Soc.*, 96, 5512 (1974). These processes accordingly are suitable for preparation of the starting compounds of the invention.

The second step of the process involves a simple hydrolysis of the 3-halo-3-lower hydrocarbonthiooxindole, advantageously in the presence of a sulfur scavenging agent. It is sufficient simply to heat the 3-halo-3-lower hydrocarbonthiooxindole in the presence of water, for example, in an aqueous solution of tetrahydrofuran. This procedure has the disadvantage, however, that a minor part of the starting material is converted to the 3,3-dithioketal. The formation of the 3,3-dithioketal can be avoided or minimized by including in the reaction mixture a sulfur scavenger, for example, mercuric oxide, and the hydrolysis can be accelerated by including in the reaction mixture a catalyst for the hydrolysis, for example, boron trifluoride etherate. The use of such sulfur scavengers and hydrolysis catalysts with different starting materials is known in the art. See, for example, Gassman et al., *J. Am. Chem. Soc.*, 96 3002 (1974). In place of mercuric oxide there can be used other mercuric salts which are known to scavenge sulfur and in place of boron trifluoride etherate, other acid catalysts can be utilised. The boron trifluoride etherate can be omitted but a longer heating time will then be required for the hydrolysis.

In the preferred form of the invention, the starting 3-lower hydrocarbonthiooxindole is dissolved in carbon tetrachloride or methylene chloride or like inert solvent and treated with a small excess of N-halosuccinimide, say, about 1.1–1.3 equivalents, without heating. The reaction will ordinarily be complete in less than twelve hours. The reaction mixture is filtered to remove the precipitate of succinimide and the filtrate evaporated to dryness. The residue is then taken up in a minimum of tetrahydrofuran or like inert solvent and the resulting solution stirred vigorously into a slurry of red mercuric oxide and boron trifluoride etherate in 20 percent tetrahydrofuran. After filtering, the reaction mixture separates into two phases which are separated. The organic phase is dried, suitably over anhydrous magnesium sulfate, and the filtrate evaporated to dryness.

The invention may be more fully understood by reference to the accompanying flow diagram, based in part on the processes of U.S. Pat. No. 3,972,894.

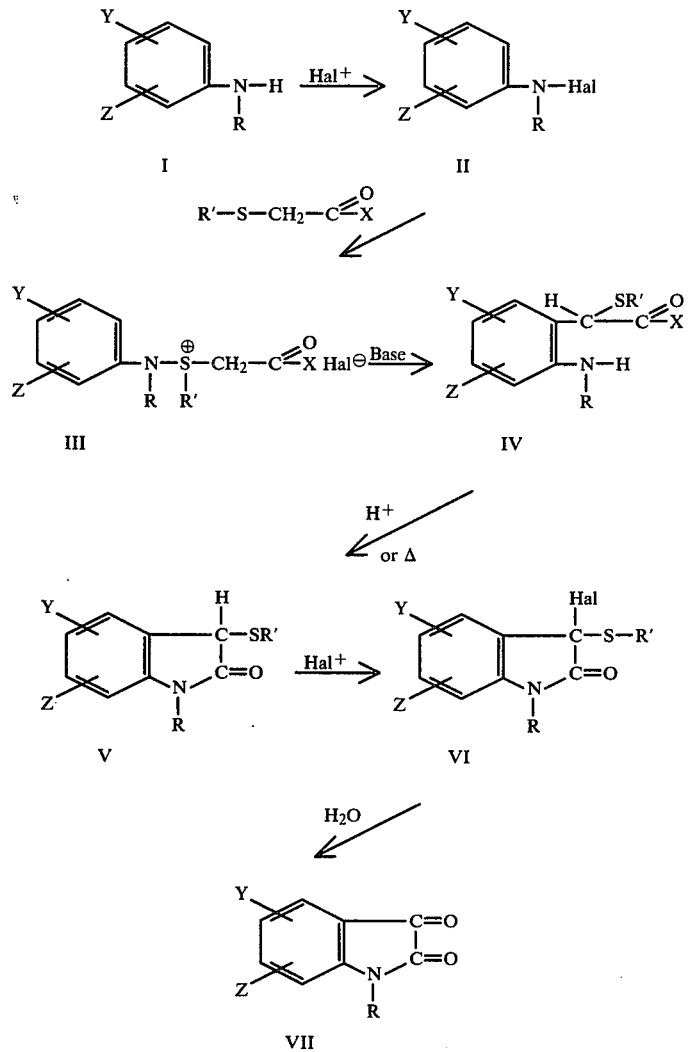

In the above formulas, X is $-OR^3$ or $-N(R^4)$, wherein $R^3$ and $R^4$ are lower hydrocarbon radicals, Y, Z, R, and R' have the same values as in U.S. Pat. No. 3,972,894. Thus, Y and Z can be hydrogen or a substituent which does not donate electrons more strongly than a methoxyl group in the meta position. Examples of the latter include halogen, e.g., chlorine bromine, nitro, cyano, lower alkyl, lower alkyloxy, lower acyloxy, a carbonyloxy-lower alkyl (carbalkoxy) and carbonyloxy-phenyl. Y and Z can also be trifluoromethyl. R can be hydrogen or a lower hydrocarbon radical free of aliphatic unsaturation. By the term "lower" is meant up to and including 8 carbon atoms. R' can be a lower hydrocarbon radical, for example, lower alkyl, phenyl, and benzyl.

DETAILED DESCRIPTION OF THE INVENTION

The following examples are given by way of illustration only. Parts and percentages are by weight unless otherwise specified.

EXAMPLE 1—ISATIN

A solution of 3-methylthiooxindole (1.70 g, 0.0095 mol) and N-chlorosuccinimide (1.34 g, 0.01 mol) in 100 ml of carbon tetrachloride was stirred at room temperature for 1 hour, the precipitate of succinimide was removed by filtration, and the filtrate was evaporated, yielding crude 3-chloro-3-methylthiooxindole. The residue, which was thus obtained, was dissolved in a minimum of tetrahydrofuran and added to a vigorously stirred slurry of red mercuric oxide powder (2.17 g, 0.01 mol) and boron trifluoride etherate (1.43 g, 0.01 mol) in 20 percent aqueous tetrahydrofuran (70 ml). After stirring at room temperature for 1 hour, 200 ml of ether was added, the reaction mixture was filtered through a pad of Celite and the organic phase of the filtrate was separated, dried over anhydrous magnesium sulfate, filtered, and this filtrate was evaporated to give isatin (1.07 g, 78%), mp 200°–202° after recrystallization from benzene.

EXAMPLE 2—5-METHYLISATIN

A solution of 5-methyl-3-methylthiooxindole (1.00 g, 0.0052 mol) and N-chlorosuccinimide (700 mg, 0.0053 mol) in carbon tetrachloride (100 ml) was stirred at room temperature for 1 hour. The precipitate was removed by filtration and the filtrate was evaporated to give the crude 3-chloro-5-methyl-3-methylthiooxindole, which was dissolved in tetrahydrofuran (20 ml) and added to a vigorously stirred slurry of red mercuric oxide (1.13 g, 0.0052 mol) and boron trifluoride etherate (745 mg, 0.0052 mol) in 70 ml of 20 percent aqueous tetrahydrofuran. After stirring at room temperature for 2 hours, the reaction mixture was filtered through a Celite pad and the filtrate was extracted with two 100-ml portions of chloroform. The chloroform extracts were dried over anhydrous magnesium sulfate, filtered, and the filtrate was evaporated. The residue was chromatographed on silica gel. Elution with chloroform gave 5-methylisatin (610 mg, 0.0038 mol, 74%), mp 185°–187° (recrystallized from ethanol) as red needles.

EXAMPLE 3—5-METHOXYISATIN

A solution of 5-methoxy-3-methylthiooxindole (420 mg, 2 mmol) and N-chlorosuccinimide (270 mg, 2 mmol) in carbon tetrachloride (74 ml) was stirred at room temperature for 1 hour. The precipitate was removed by filtration and the filtrate was evaporated to dryness, yielding crude 3-chloro-5-methoxy-3-methylthiooxindole. The residue was dissolved in tetrahydrofuran (10 ml) and added to a vigorously stirred slurry of red mercuric oxide (435 mg, 2 mmol) and boron trifluoride etherate (290 mg, 2 mmol) in aqueous 20 percent tetrahydrofuran (40 ml). The reaction mixture was stirred at room temperature for 1 hour. The reaction mixture was filtered through a pad of Celite and the filtrate was extracted with chloroform. The organic layer was dried over anhydrous magnesium sulfate, filtered, and the filtrate was concentrated. The residue was purified by column chromatography on silica gel to give 5-methoxyisatin (287 mg, 81%), mp 202°–204° (recrystallized from benzene).

EXAMPLE 4—PART 4-A- 5-CHLORO-3-METHYLTHIOOXINDOLE

On a 0.055 mol scale p-chloroaniline was converted to 5-chloro-3-methylthiooxindole according to the general procedure of Gassman and van Bergen, supra. Recrystallization of the crude oxindole from methanol gave pure product (9.10 g, 77.5%), mp 171°–173° (recrystallized from methanol); ir (KBr) 3100 (NH) and 1705 cm$^{-1}$ (C=O); nmr (DMSO-d$_6$) $\tau$ —1.40 (b s, 1H, NH), 2.70 (m, 2H, H$_4$ and H$_6$), 3.20 (d, 1H, J$_{6,7}$=8 Hz, H$_7$), 5.50 (s, 1H, H$_3$) and 8.05 (s, 3H, 3-SCH$_3$).

Anal. Calcd. for C$_9$H$_8$ClNOS: C, 50.58; H, 3.73; N, 6.56. Found: C, 50.59; H, 3.83; N, 6.51.

EXAMPLE 4—PART 4-B- 5-CHLOROISATIN

A solution of 5-chloro-3-methylthiooxindole (1.35 g, 6.3 mmol) and N-chlorosuccinimide (950 mg, 7 mmol) in carbon tetrachloride (100 ml) was refluxed for 1 hour, cooled, and the precipitate was removed by filtration. The filtrate was concentrated to dryness, yielding crude 3,5-dichloro-3-methylthiooxindole. The residue was dissolved in 25 ml of tetrahydrofuran and added rapidly to a vigorously stirred slurry of red mercuric oxide (1.37 g, 6.3 mmol) and boron trifluoride etherate (900 mg, 6.3 mmol) in 100 ml of 20 percent aqueous tetrahydrofuran. After stirring for 3 hours, the solution was filtered through a pad of Celite and the filtrate was extracted with chloroform. The chloroform extracts were dried over anhydrous magnesium sulfate, filtered and the filtrates were concentrated to give a red solid which was chromatographed on silica gel with chloroform as the eluent. There was obtained 5-chloroisatin (850 mg, 75%), mp 248°–251° (recrystallized from ethanol).

EXAMPLE 5—PART 5-A-5-CARBOETHOXY-3-METHYLTHIOOXINDOLE

On a 0.05 mol scale ethyl p-aminobenzoate was converted to 5-carboethoxy-3-methylthiooxindole according to the procedure of Gassman and van Bergen, supra. The reaction gave 9.20 g (73 percent of the desired oxindole), mp 151°–153° (recrystallized from benzene); ir (KBr) 3240 (NH), 1735 (C=O) and 1695 cm$^{-1}$ (C=O); nmr (CDCl$_3$) $\tau$ 0.20 (1H, b s, NH), 2.00 (d, 1H, J$_{4,6}$<1 Hz, H$_4$), 2.10 (d of d, 1H, J$_{4,6}$<1 Hz, J$_{6,7}$=8 Hz, H$_6$), 3.05 (d, 1H, J$_{6,7}$=8 Hz, H$_7$), 5.50 (q, 2 H, CO$_2$CH$_2$CH$_3$), 5.70 (s, 1H, H$_3$), 8.00 (s, 3H, SCH$_3$), 8.60 (t, 3H, CO$_2$CH$_2$CH$_3$).

Anal. Calcd for C$_{12}$H$_{13}$NO$_3$S: C, 57.35; H, 5.21; N, 5.57. Found: C, 57.36; H, 5.19; N, 5.49.

EXAMPLE 5—Part 5-B-5-CARBOETHOXYISATIN

A solution of 5-carboethoxy-3-methylthiooxindole (1.50 g, 7 mmol) and N-chlorosuccinimide (1.25 g, 9.3 mmol) in methylene chloride (150 ml) was stirred at room temperature for 24 hours. The solvent was removed in vacuo, yielding crude 3-chloro-5-carboethoxy-3-methylthiooxindole and the residue was dissolved in tetrahydrofuran and added to a vigorously stirred slurry of red mercuric oxide (1.53 g, 7 mmol) and boron trifluoride etherate (1.00 g, 7 mmol) in 100 ml of 50 percent aqueous tetrahydrofuran. After stirring at room temperature for 1 hour, the red solution was extracted with chloroform. The organic extracts were dried over anhydrous magnesium sulfate, filtered, evaporated, and the residue was chromatographed on silica gel. Elution with chloroform gave 5-carboethoxyisatin (860 mg, 56%) as a yellow solid, mp 205°–207° (recrystallized from ether), ir (KBr) 3265 (NH), 1765 (ester C=O), 1750 (C=O), and 1700 cm$^{-1}$ (amide C=O); nmr (DMSO-d$_6$) $\tau$ —1.00 (1H, b, s, NH), 1.80 (d of d, 1H, J$_{4,6}$=2 Hz, J$_{6,7}$=9 Hz, H$_6$), 1.90 (d, 1H, J$_{4,6}$=2H$_3$, H$_4$), 3.20 (d, 1H, J$_{6,7}$=9Hz, H$_7$), 5.65 (q, 2H, CO$_2$CH$_2$CH$_3$), and 8.60 (t, 3H, CO$_2$CH$_2$CH$_3$); mass spectrum m/e obs. 219.0534 (calc. 219.0531).

Anal. Calcd for C$_{11}$H$_9$NO$_4$: C, 60.27; H, 4.14; N, 6.39. Found: C, 60.23; H, 4.18; N, 6.51.

EXAMPLE 5—PART 5-C-5,5'-DICARBOETHOXYINDIGO

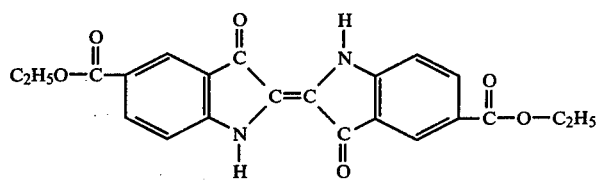

By reacting 5-carboethoxyisatin with phosphorous trichloride, phosphorous, and acetyl chloride by the method of Baeyer, 5,5'-dicarboethoxyindigo, useful as a dyestuff, is obtained.

EXAMPLE 5—PART 5-D-5'-CARBOETHOXY-2'-INDOLE-2-THIANAPHTHENE INDIGO

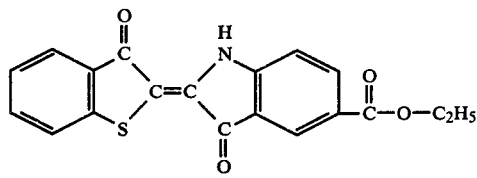

By reacting 5-carboethoxyisatin with phosphorous pentachloride, there is obtained 5-carboethoxyisatin chloride which, on reaction with 3(2H)-thianaphthenone, yields 5'-carboethoxy-2'-indole-2-thianaphthenone indigo, which also is useful as a dyestuff.

EXAMPLE 6—PART 6-A-5-CYANO-3-METHYLTHIOOXINDOLE

Utilizng the general procedure for the synthesis of oxindoles, as described by Gassman and van Bergen, supra, p-cyanoaniline ws converted into 5-cyano-3-methylthiooxindole on a 0.0466 mol scale. Recrystallization from methanol gave the pure oxindole (7.30 g, 80% yield) mp 182°-183°; ir (KBr) 3100 (NH), 2220 (C≡N) and 1720 cm$^{-1}$ (C=O), nmr (DMSO-d$_6$) τ −1.00 (b s 1H, NH), 2.27 (d of d, 1H, J$_{4,6}$=2 Hz, J$_{6,7}$=9 Hz, H$_6$), 2.31 (d, 1H, J$_{4,6}$=2 Hz, H$_4$), 3.00 (d, 1H, J$_{6,7}$=9 Hz, H$_7$), 5.34 (s, 1H, H$_3$), 7.97 (s, 3H, SCH$_3$).

Anal. Calcd for C$_{10}$H$_8$N$_2$OS: C, 58.80; H, 3.95; N, 13.72. Found: C, 58.65; H, 4.06; N, 13.40.

EXAMPLE 6—PART 6-B-5-CYANOISATIN

A solution of 5-cyano-3-methylthiooxindole (950 mg, 4.66 mmol) and N-chlorosuccinimide (800 mg, 5.95 mmol) in 100 ml of methylene chloride was stirred at room temperature for 24 hours. The solvent was removed in vacuo, yielding 3-chloro-5-cyano-3-methylthiooxindole and the residue, which was dissolved in a minimum of tetrahydrofuran, was added to a vigorously stirred slurry of red mercuric oxide (1.00 g, 4.7 mmol) and boron trifluoride ethereate (670 mg, 4.7 mmol) in 100 ml of 50 percent aqueous tetrahydrofuran. After 2 hours, the reaction mixture was filtered through a pad of Celite. The pad was washed with three 100-ml portions of chloroform. The organic layer was separated, dried over anhydrous magnesium sulfate, filtered, and the filtrate was evaporated. The residue was chromatographed on silica gel. Elution with chloroform-ethanol (9:1 v/v) gave 5-cyanoisatin as an orange solid (525 mg, 65%), mp 270°-272° (dec); ir (KBr) 3100 (NH), 2220 (C≡N), 1730 (C=O) and 1710 cm$^{-1}$ (C=O); nmr (DMSO-d$_6$)τ −1.30 (1H, b, s, NH), 2.00 (d of d, 1H, J$_{4,6}$=2 Hz, J$_{6,7}$=8.5 Hz, H$_6$), 2.10 (d, 1H, J$_{4,6}$=2 Hz, H$_4$), and 2.90 (d, 1H, J$_{6,7}$=8.5 Hz, H$_7$); mass spectrum, m/e obs. 172.0238 (calc. 172.0272).

Anal. Calcd for C$_9$H$_4$N$_2$O$_2$: C, 62.80; H, 2.34; N, 16.28. Found: C, 62.37; H, 2.41; N, 1607.

EXAMPLE 6—PART 6-C-5,5'-DICYANOINDIGO

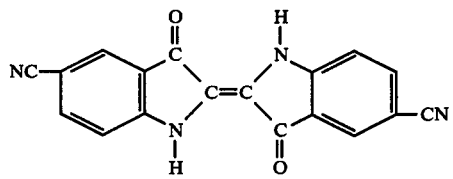

By reacting 5-cyanoisatin with phosphorous trichloride, phosphorous, and acetylchloride by the method of Baeyer, (Indigoid Dyes, supra, p558), 5,5'-dicyanoindigo, useful as a dyestuff is obtained.

EXAMPLE 6—PART 6-D-5'-CYANO-2'-INDOLE-2-THIANAPHTHENE INDIGO

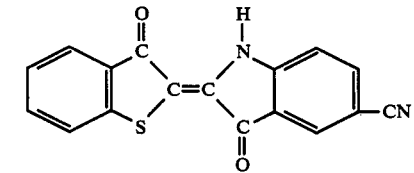

By reacting 5-cyanoisatin with phosphorous pentachloride, there is obtained 5-cyanoisatin chloride which, on reaction with 3(2H)-thianaphthenone, yields 5'-cyano-2'-indole-2-thianaphthenone indigo, which also is useful as a dyestuff.

EXAMPLE 7—5-NITROISATIN

A solution of 3-methylthio-5-nitrooxindole (900 mg, 4 mmol) and N-chlorosuccinimide (600 mg, 4.5 mmol) in 50 ml of chloroform was stirred at room temperature for 1 hour and then evaporated to dryness in vacuo, yielding 3-chloro-3-methylthio-5-nitrooxindole. The residue was dissolved in 15 ml of tetrahydrofuran and added to a vigorously stirred slurry of red mercuric oxide powder (900 mg, 4.3 mmol) and boron trifluoride etherate (600 mg, 4.3 mmol) in 100 ml of 20 percent aqueous tetrahydrofuran. After stirring at room temperature for two hours, the reaction mixture was extracted with three 100-ml portions of chloroform. The chloroform layer was dried over anyhdrous magnesium sulfate, filtered and evaporated. The residue was recrystallized from 95 percent ethanol to give 5-nitroisatin (600 mg, 78%), mp 252°-254°

EXAMPLE 8—PART 8-A-3-METHYLTHIO-5-TRIFLUOROMETHYLOXINDOLE

Utilizing the general procedure of Gassman and van Bergen, supra, p-trifluoromethylaniline was converted to 3-methylthio-5-trifluoromethyloxindole on a 0.0124 mol scale. Recrystallization of the product from cyclohexane gave pure 3-methylthio-5-trifluoromethyloxindole (2.32 g, 76%), mp 139.0°–140.5° (recrystallized from cyclohexane); ir (KBr) 3200 (NH) and 1730 cm$^{-1}$ (C=O); nmr (CDCl$_3$) $\tau$ 0.57 (b s, 1H, NH), 2.37 (d, 1H, $J_{4,6}=1$ Hz, H$_4$), 2.47 (d of d, $J_{4,6}=1$ Hz, $J_{6,7}=8$ Hz, H$_6$), 3.00 (d, 1H, $J_{6,7}=8$ Hz), 5.67 (s, 1H, H$_3$) and 7.90 (s, 3H, 3-SCH$_3$).

Anal. Calcd for C$_{10}$H$_8$F$_3$NOS: C, 48.58; H, 3.26; N, 5.67. Found: C, 48.48; H, 3.29; N, 5.58.

EXAMPLE 8—PART 8-B-5-TRIFLUOROMETHYLISATIN

A solution of 3-methylthio-5-trifluoromethyloxindole (1.40 g, 0.0057 mol) and N-chlorosuccinimide (800 mg, 0.006 mol) in 100 ml of carbon tetrachloride was stirred at room temperature for 1 hour. The precipitated succinimide was removed by filtration, and the filtrate was evaporated to give 3-chloro-3-methylthio-5-trifluoromethyl oxindole as a yellow solid which was dissolved in 30 ml of tetrahydrofuran and added to a vigorously stirred slurry of red mercuric oxide (1.30 g, 5.8 mmol) and boron trifluoride etherate (860 mg, 5.8 mmol) in 100 ml of 20 percent aqueous tetrahydrofuran. The resulting mixture was stirred for 2 hours at room temperature, filtered through a pad of Celite and the filtrate was extracted with four 100-ml portions of methylene chloride. The methylene chloride extracts were dried over anhydrous magnesium sulfate, filtered, and evaporated to give a residue which was chromatographed on silica gel. Elution with methylene chloride gave 5-trifluoromethylisatin as yellow needles (860 mg, 73%), mp 191°–193° (recrystallized from benzene); ir (KBr) 3200 (NH), 1750 (C=O), 1710 cm$^{-1}$ (C=O); nmr (DMSO-d$_6$), $\tau$ −1.20 (b s, 1H, NH), 2.15 (d, 1H, H$_6$), 2.30 (s, 1H, H$_4$), 2.90 (d, 1H, $J_{6,7}=8$ Hz, H$_7$); mass spectrum m/e obs. 215.0196 (calc. 215.0194).

Anal. Calcd for C$_9$H$_4$F$_3$NO$_2$: C, 50.24; H, 1.87; N, 6.51. Found: C, 50.12; H, 1.92; N, 6.43.

A phenylhydrazone derivative of 5-trifluoromethylisatin was prepared, mp 263°–265°; mass spectrum m/e obs. 305.0767 (calc. for C$_{15}$H$_{10}$F$_3$N$_3$O 305.0776).

EXAMPLE 8—PART 8-C-5,5'-TRIFLUOROMETHYLINDIGO

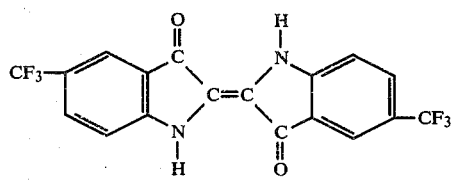

By reacting 5-trifluoromethylisatin with phosphorous trichloride, phosphorous, and acetyl chloride by the method of Baeyer, 5,5'-trifluoromethylindigo, useful as a dyestuff, is obtained.

EXAMPLE 8—PART 8-D-5'-TRIFLUOROMETHYL-2'-INDOLE-2-THIANAPHTHENE INDIGO

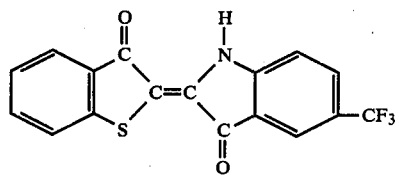

By reacting 5-trifluoromethylisatin with phosphorus penta-chloride, there is obtained 5-trifluoromethylisatin chloride which, on reaction with 3(2H)-thianaphthenone, yields 5'-trifluoromethyl-2'-indole-2-thianaphthenone indigo, which also is useful as a dyestuff.

EXAMPLE 9—PART 9-A-4-NITROISATIN

A solution of 3-methylthio-4-nitrooxindole (1.58 g, 7 mmol) and N-chlorosuccinimide (1.20 g, 9 mmol) in 100 ml of methylene chloride was stirred at room temperature for 48 hours. The solvent was removed in vacuo, yielding crude 3-chloro-3-methylthio-4-nitrooxindole. The residue was dissolved in 25 ml of tetrahydrofuran and added rapidly to a vigorously stirred slurry of red mercuric oxide (1.52 g, 7 mmol) and boron trifluoride etherate (1.00 g, 7 mmol) in 100 ml of 50 percent aqueous tetrahydrofuran. After stirring for 3 hours, the solution was filtered through a Celite pad which was then washed with copious amounts of chloroform. The organic layer was separated, dried over anhydrous magnesium sulfate, filtered, and the filtrate was evaporated. The residue was chromatographed on silica gel. Elution with chloroform-ethanol (9:1) gave 4-nitroisatin (535 mg, 40%), mp 248°–250° (dec) (recrystallized from ethanol); ir (KBr) 3200 (NH), 1750 (C=O), 1710 (C=O), 1520 (NO$_2$) and 1350 cm$^{-1}$ (NO$_2$); nmr (DMSO-d$_6$) $\tau$ −1.30 (1H, b s, NH), 2.20–2.80 (m, 3H, aryl H).

Anal. Calcd for C$_8$H$_4$N$_2$O$_4$: C, 50.00; H, 2.10; N, 14.58. Found: C, 49.93; H, 2.27; N, 14.46.

EXAMPLE 9—PART 9-B-4,4'-DINITROINDIGO

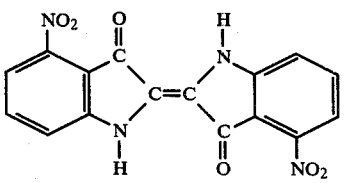

By reacting 4-nitroisatin with phosphorous trichloride, phosphorous, and acetyl chloride by the method of Baeyer, 4,4'-dinitroindigo, useful as a dyestuff, is obtained.

EXAMPLE 9—PART 9-C-5,6,7-TRICHLORO-4'-NITRO-2'-INDOLE-2-THIANAPHTHENE INDIGO

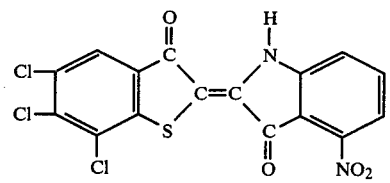

By reacting 4-nitroisatin with phosphorous pentachloride, there is obtained 5,6,7-trichloro-4'-nitroisatin chloride which, on reaction with 5,6,7-trichloro 3(2H)-thianaphthenone, yields 5,6,7-trichloro-4'nitro-2'-indole-2-thianaphthene indigo, which also is useful as a dyestuff.

EXAMPLE 10—PART 10-A-7-METHYLISATIN

A solution of 7-methyl-3-methylthiooxindole (1 g, 0.0052 mol) and N-chlorosuccinimide (0.7 g, 0.0052 mol) in chloroform (100 ml) was stirred at room temperature for 1 hour. The solution was evaporated, yielding crude 3-chloro-7-methyl-3-methylthiooxindole, and the residue was dissolved in a minimum amount of tetrahydrofuran (ca. 10 ml) and added to a vigorously stirred slurry of red mercuric oxide (1.13 g, 0.0052 mol) and boron trifluoride ethereate (0,75, 0.0054 mol) in 50 ml of 20 percent aqueous tetrahydrofuran. After stirring at room temperature for 1 hour, 150 ml of ether was added, the reaction mixture was filtered through a pad of Celite, and the organic phase of the filtrate was separated, dried over anhydrous magnesium sulfate, filtered, and the solvent was evaporated. The red residue was recrystallized from methanol to give 0.6 g (71%) 7-methylisatin, mp 267°-269°.

EXAMPLE 10—PART 10-B-7,7'-DIMETHYLINDIGO

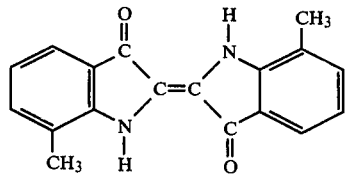

By reacting 7-methylisatin with phosphorous trichloride, phosphorous, and acetyl chloride by the method of Baeyer, 7,7'-dimethylindigo, useful as a dyestuff, is obtained.

EXAMPLE 10 PART 10—C-5,6,7-TRICHLORO-7'-METHYL-2'-INDOLE-2-THIANAPHTHENE INDIGO

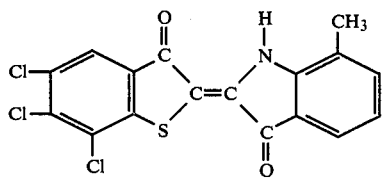

By reacting 7-methylisatin with phosphorous pentachloride, there is obtained 7-methylisatin chloride which, on reaction with 5,6,7-trichloro 3(2H)-thianaphtheneone, yields 5,6,7-trichloro-7'-methyl-2'-indole-2-thianaphthene indigo, which also is useful as a dyestuff.

EXAMPLE 11—1-METHYLISATIN

A solution of 1-methyl-3-methylthiooxindole (1.07 g, 5.56 mmol) and N-chlorosuccinimide (800 mg, 6.0 mmol) in 75 ml of carbon tetrachloride was stirred at room temperature for 1 hour, filtered, and the filtrate was evaporated to give a residue yielding 3-chloro-1-methyl-3-methylthiooxindole. The residue was dissolved in 20 ml of tetrahydrofuran and rapidly added to a vigorously stirred slurry of red mercuric oxide (1.20 g, 5.56 mmol) and boron trifluoride etherate (790 mg, 5.56 mmol) in 75 mol of 20 percent aqueous tetrahydrofuran. After stirring at room temperature for 1 hour, the reaction mixture was filtered through a Celite pad and the filtrate was extracted with ether. Evaporation of the ether layer gave a residue which was purified by chromatography on silica gel. Elution with methylene chloride gave 1-methylisatin (550 mg, 61%), mp 131°-133°; nmr (CDCl$_3$) $\tau$ 2.23-2.60 (m, 2H, aromatic H), 2.71-2.90 (m, 2H, aromatic H and 6.70 (s, 3H, N—CH$_3$).

EXAMPLE 12—ISATIN AND 3,3-DI(METHYLTHIO)OXINDOLE

A solution of 3-methylthiooxindole (1.79 g, 0.01 mol) and N-chlorosuccinimide (1.45 g, 0.011 mol) in 100 ml of carbon tetrachloride was stirred at room temperature for 1 hour. The precipitated succinimide was removed by filtration and the filtrate was evaporated to dryness on a rotary evaporator. The residue was boiled in 100 ml of 20 percent aqueous tetrahydrofuran for 6 hours, cooled, and the solution was extracted with chloroform. The chloroform extract was dried over anhydrous magnesium sulfate, filtered and evaporated. The residue was chromatographed on silica gel. Elution with chloroform gave 3,3-di(methylthio)oxindole (560 mg, 24%), mp 163°-164° (recrystallized from benzene); ir (KBr), 3180 (NH) and 1700 cm$^{-1}$ (C=O); nmr (CDCl$_3$), $\tau$ 0.98 (b s, 1H, NH), 2.87 (m, 4H, aryl H), and 7.83 (s, 6H, SCH$_3$).

Anal. Calcd for C$_{10}$H$_{11}$NOS$_2$: C, 53.30; H, 4.92; N, 6.22. Found: C, 53.00; H, 5.01; N, 6.12.

Further elution with chloroform gave isatin (1.00 g, 68%), mp 200°-202° (recrystallized from benzene).

On hydrolysis in the presence of red mercuric oxide and boron trifluoride etherate in 20 percent aqueous tetrahydrofuran, 3,3-di(methylthio)oxindole is converted to isatin.

EXAMPLE 13-5-METHOXYISATIN AND 3,3-DI(METHYLTHIO)-5-METHOXYOXINDOLE

A suspension of 5-methoxy-3-methylthiooxindole (1.00 g, 4.8 mmol) and N-chlorosuccinimide (650 mg, 4.8 mmol) was refluxed for 1 hour in 100 ml of carbon tetrachloride. The cooled solution was filtered and the filtrate was evaporated to give a residue which was refluxed in 100 ml of 20 percent aqueous tetrahydrofuran for 18 hours. After cooling, the dark solution was extracted with chloroform. The chloroform layer was separated, dried over anhydrous magnesium sulfate, filtered and the filtrate was evaporated. The residue was chromatographed on silica gel. Elution with chloroform gave 3,3-di(methylthio)-5-methoxyoxindole (300 mg, 24%), mp 167-169 (recrystallized from benzene); ir (KBr), 3200 (NH), and 1705 cm$^{-1}$ (C=O); nmr (CDCl$_3$) τ 0.65 (b s, 1H, NH), 3.10 (m, 2H, H$_6$ and H$_7$), 3.16 (d, 1H, J$_{4,6}$=2 Hz, H$_4$), 6.20 (s, 3H, OCH$_3$) and 7.80 (s, 6H, SCH$_3$); mass spectrum m/e obs. 255.0382 (calc. 255.0387).

Anal. Calcd for C$_{11}$H$_{13}$NO$_2$S$_2$: C, 51.74; H, 5.13; N, 5.49. Found: C, 51.88; H, 5.19; N, 5.42.

Further elution with chloroform gave 5-methoxyisatin (525 mg, 62%), mp 202°–204°.

On hydrolysis in the presence of red mercuric oxide and boron trifluoride etherate in 20 percent aqueous tetrahydrofuran, 3,3-di(methylthio)-5-methoxyoxindole is converted to 5-methoxyisatin.

EXAMPLE 14—5-METHYLISATIN AND 3,3-DI(METHYLTHIO)-5-METHYLOXINDOLE

A solution of 5-methyl-3-methylthiooxindole (1.00 g, 5.2 mmol) and N-chlorosuccinimide (700 mg, 5.5 mmol) in 100 ml of carbon tetrachloride was stirred at room temperature for 1 hour, filtered to remove the succinimide, and the solvent was removed in vacuo. The residue was dissolved in 100 ml of 20 percent aqueous tetrahydrofuran and refluxed for 5 hours. After cooling, the reaction mixture was extracted with three 100-ml portions of chloroform. The chloroform extracts were dried over anhydrous magnesium sulfate, filtered, and the filtrate was evaporated to give a residue which was chromatographed on silica gel. Elution wich chloroform gave 3,3-di(methylthio)-5-methyloxindole (172 mg, 14%), mp 188°–189° (recrystallized from methanol); ir (KBr) 3170 (NH) and 1705 cm$^{-1}$ (C=O); nmr (CDCl$_3$) τ 0.60 (1H, b s, NH), 2.80–3.20 (3H, m, aryl H), 7.75 (3H, s, 5-CH$_3$) and 8.00 (6H, s, SCH$_3$); mass spectrum m/e obs. 239.0460 (calc. 239.0438).

Further elution with chloroform gave 5-methylisatin (525 mg, 63%), mp 185°–187° (recrystallized from 95% ethanol).

On hydrolysis in the presence of red mercuric oxide and boron trifluoride etherate in 20 percent aqueous tetrahydrofuran, 3,3-di-(methylthio)-5-methyloxindole is converted to 5-methylisatin.

EXAMPLE 15—5-CHLORO-3,3-DI(METHYLTHIO)OXINDOLE AND 5-CHLOROISATIN

A solution of 5-chloro-3-methylthiooxindole (1.35, 6.3 mmol) and N-chlorosuccinimide (935 mg, 7.0 mmol) in 100 ml of carbon tetrachloride was refluxed for 1 hour, cooled, and the precipitated succinimide was removed by filtration. The filtrate was evaporated and the residue was dissolved in 100 ml of 20 percent aqueous tetrahydrofuran and refluxed for 18 hours. After cooling, the reaction mixture was extracted with two 100-ml portions of chloroform. The oganic solution was dried over anhydrous magnesium sulfate, filtered, and the filtrate was evaporated. The residual solid was chromatographed on silica gel. Elution with methylene chloride gave 5-chloro-3,3-di(dimethylthio)oxindole (200 mg, 12%), mp 222°–224° (recrystallized from ethanol); ir (KBr) 3150 (NH) and 1700 cm$^{-1}$ (C=O); nmr (CDCl$_3$) τ −0.25 (1H, b s, NH), 2.75 (1H, d, J$_{6,7}$=8 Hz, H$_7$) 2.80 (1H, m, H$_6$), 3.10 (m, 1H, H$_4$), 7.83 (s, 6H, SCH$_3$); mass spectrum m/e obs. 258.9897 (calc. 258.9892).

Anal. Calcd for C$_{10}$H$_{10}$NOClS: C, 46.23; H, 3.88; N, 5.39. Found: C, 46.44; H, 4.02; N, 5.28.

Further elution with methylene chloride gave 5-chloroisatin (770 mg, 68%), mp 249°–252° (recrystallized from ethanol).

On hydrolysis in the presence of red mercuric oxide and boron trifluoride etherate in 20 percent aqueous tetrahydrofuran, 5-chloro-3,3-di(methylthio)oxindole is converted to 5-chloroisatin.

It is to be understood that the invention is not to be limited to the exact details of operation or structure shown and described, as obvious modifications and equivalents will be apparent to one skilled in the art.

We claim:

1. A process for making isatins which comprises the steps of
   (1) subjecting a 3-hydrocarbonthiooxindole, having a hydrogen atom present as a further substituent on the 3-carbon atom thereof, to oxidative halogenation by reaction with an oxidating-halogenating agent under oxidative-halogenation reaction conditions to produce a 3-halo-3-hydrocarbon thiooxindole;
   (2) subjecting the formed 3-halo-3-hydrocarbonthiooxindole to hydrolysis with a hydrolyzing agent under hydrolysis conditions to produce an isatin; and,
   (3) isolating the thus-formed isatin.

2. The process of claim 1, in which the 3-hydrocarbonthiooxindole has the formula

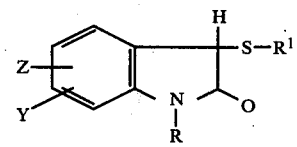

wherein
Y and Z are hydrogen, halogen, nitro, cyano, trifluoromethyl, lower alkyl, lower alkoxy, lower acyloxy, carbonyloxy-lower alkyl, or carboxyloxyphenyl;
R is hydrogen or a hydrocarbon radical free of aliphatic unsaturation containing 1 to 8 carbon atoms, inclusive and
R$^1$ is lower alkyl, phenyl, or benzyl.

3. The process of claim 2, in which the oxidative halogenation is effected with N-chlorosuccinimide.

4. The process of claim 2, in which the hydrolysis is effected in the presence of a sulfur scavenging agent.

5. The process of claim 2, in which the hydrolysis is effected in aqueous tetrahydrofuran without a sulfur scavenger.

6. The process of claim 4, in which the scavenging agent is mercuric oxide.

7. The process of claim 2, in which the hydrolysis is effected in the presence of a hydrolysis catalyst.

8. The process of claim 4, in which the hydrolysis is effected in the presence of a hydrolysis catalyst.

9. The process of claim 6, in which the hydrolysis is effected in the presence of boron trifluoride etherate.

10. The compound of the formula

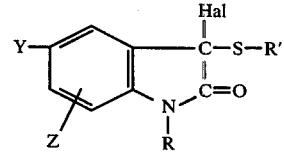

wherein

X and Z are hydrogen, halogen, nitro, cyano, trifluoromethyl, lower alkyl, lower alkoxy, lower acyloxy, carbonyloxyl-lower alkyl, or carboxyloxy-phenyl;

R is hydrogen or a lower hydrogenated radical free of aliphatic unsaturation;

R' is a lower hydrocarbon radical; and

Hal is chlorine or bromine.

11. The compound of claim 10, 3-chloro-3-methylthiooxindole.

12. The compound of claim 10, 3-chloro-5-methyl-3-methylthiooxindole.

13. The compound of claim 10, 3-chloro-5-methoxy-3-methylthiooxindole.

14. The compound of claim 10, 3,5-dichloro-3-methylthiooxindole.

15. The compound of claim 10, 3-chloro-5-carboethoxy-3-methylthiooxindole

16. The compound of claim 10, 3-chloro-5-cyano-3-methylthiooxindole.

17. The compound of claim 10, 3-chloro-3-methylthio-5-nitrooxindole.

18. The compound of claim 10, 3-chloro-3-methylthio-5-trifluoromethyloxindole.

19. The compound of claim 10, 3-chloro-3-methylthio-4-nitrooxindole.

20. The compound of claim 10, 3-chloro-7-methyl-3-methylthiooxindole.

21. The compound of claim 10, 3-chloro-1-methyl-3-methylthiooxindole.

22. A compound of the formula

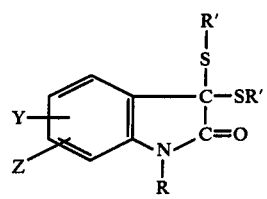

wherein

Y and Z are hydrogen, halogen, nitro, cyano, trifluoromethyl, lower alkyl, lower alkoxy, lower acyloxy carbonyloxy-lower alkyl, or carboxyloxy-phenyl;

R is hydrogen or a lower hydrogenated radical free of aliphatic unsaturation; and R' is lower hydrocarbon.

23. The compound of claim 22, 3,3-di(methylthio)oxindole.

24. The compound of claim 22, 3,3-di(methylthio)-5-methoxyoxindole.

25. A process which comprises the step of subjecting a 3-hydrocarbonthiooxindole, having a hydrogen atom present as a further substituent on the 3-carbon atom thereof, to oxidative halogenation by reaction with an oxidating-halogenating agent under oxidative-halogenation reaction conditions to produce a 3-halo-3-hydrocarbonthiooxindole.

* * * * *

UNITED STATES PATENT AND TRADEMARK OFFICE
CERTIFICATE OF CORRECTION

PATENT NO. : 4,188,325

DATED : February 12, 1980

INVENTOR(S) : Paul G. Gassman and Berkeley W. Cue, Jr.

It is certified that error appears in the above—identified patent and that said Letters Patent is hereby corrected as shown below:

[73] Assignee; "Regents of University of Minnesota" should read -- Regents of the University of Minnesota --

Col. 8, line 65; "anyhdrous" should read -- anhydrous --

Col. 13, line 53; "oganic" should read -- organic --

Col. 14, line 37; "carboxyloxy-" should read -- carbonyloxy- --

Col. 15, lines 3 & 4; "carboxyloxy-phenyl" should read -- carbonyloxy-phenyl --

Col. 15, line 18; "methylthiooxindole" should have a period (.) inserted after it.

Col. 16, lines 15 & 16; "carboxyloxy-phenyl" should read -- carbonyloxy-phenyl --

UNITED STATES PATENT AND TRADEMARK OFFICE
CERTIFICATE OF CORRECTION

PATENT NO. : 4,188,325
DATED : February 12, 1980
INVENTOR(S) : Paul G. Gassman and Berkeley W. Cue, Jr.

It is certified that error appears in the above—identified patent and that said Letters Patent is hereby corrected as shown below:

Col. 3, line 5; "percent tetrahydrofuran" should read -- percent aqueous tetrahydrofuran --
Col. 5, line 58; "-$d_6$)" should read -- -$d_{-6}$) --
Col. 6, line 61; "-$d_6$)" should read -- -$d_{-6}$) --
Col. 6, line 61; "1H, b, s," should read -- 1H, b s, --
Col. 7, line 37; "Utilizng" should read -- Utilizing --
Col. 7, line 39; "ws" should read -- was --
Col. 7, line 43; "-$d_6$)" should read -- -$d_{-6}$) --
Col. 8, line 2; "-$d_6$)τ-1.30 (1H, b, s," should read -- -$d_{-6}$)τ-1.30 (1H, b s,--
Col. 9, line 44; "-$d_6$)" should read -- -$d_{-6}$) --
Col. 10, line 47; "-$d_6$)" should read -- -$d_{-6}$) --
Col. 11, line 68 & Col. 12, line 1; "thianaphtheneone" should read -- thianaphthenone --
Col. 13, line 27; "wich" should read -- with --

Signed and Sealed this

Sixteenth Day of September 1980

[SEAL]

Attest:

SIDNEY A. DIAMOND

Attesting Officer

Commissioner of Patents and Trademarks